United States Patent [19]
Horwell et al.

[11] Patent Number: 6,103,932
[45] Date of Patent: Aug. 15, 2000

[54] SUBSTITUTED CYCLIC AMINO ACIDS AS PHARMACEUTICAL AGENTS

[75] Inventors: David Christopher Horwell, Foxton; Justin S. Bryans, Balsham; Clare O. Kneen, Little Walden; Andrew I. Morrell, Huntingdon; Giles S. Ratcliffe, Near Royston, all of United Kingdom; Johannes Hartenstein, Stegen-Wittental, Germany

[73] Assignee: Warner-Lambert Company, Morris Plains, N.J.

[21] Appl. No.: 09/068,874

[22] PCT Filed: Feb. 18, 1997

[86] PCT No.: PCT/US97/02295

§ 371 Date: May 20, 1998

§ 102(e) Date: May 20, 1998

[87] PCT Pub. No.: WO97/33858

PCT Pub. Date: Sep. 18, 1997

Related U.S. Application Data

[60] Provisional application No. 60/013,432, Mar. 14, 1996.

[51] Int. Cl.[7] ......................... C07C 61/08; A61K 31/195
[52] U.S. Cl. .......................... 562/507; 562/508; 514/561
[58] Field of Search .................................. 562/507, 508; 514/561

[56] References Cited

U.S. PATENT DOCUMENTS

| | | | |
|---|---|---|---|
| 4,024,175 | 5/1977 | Satzinger et al. | 560/122 |
| 4,087,544 | 5/1978 | Satzinger et al. | 514/530 |
| 4,152,326 | 5/1979 | Hartenstein et al. | 546/16 |
| 4,894,476 | 1/1990 | Butler et al. | 562/504 |
| 4,956,473 | 9/1990 | Mettler et al. | 548/408 |
| 4,958,044 | 9/1990 | Mettler et al. | 558/431 |
| 4,960,931 | 10/1990 | Butler et al. | 562/507 |
| 5,025,035 | 6/1991 | Wallace | 514/530 |
| 5,068,413 | 11/1991 | Steiner et al. | 562/507 |
| 5,084,479 | 1/1992 | Woodruff | 514/530 |
| 5,091,567 | 2/1992 | Geibel et al. | 562/507 |
| 5,095,148 | 3/1992 | Mettler et al. | 562/507 |
| 5,098,931 | 3/1992 | Duggan et al. | 514/460 |
| 5,130,455 | 7/1992 | Mettler et al. | 558/426 |
| 5,132,451 | 7/1992 | Jennings et al. | 562/507 |
| 5,136,091 | 8/1992 | Mettler et al. | 562/507 |
| 5,149,870 | 9/1992 | Mettler et al. | 562/507 |
| 5,319,135 | 6/1994 | Jennings et al. | 562/507 |
| 5,362,883 | 11/1994 | Jennings et al. | 548/408 |
| 5,436,343 | 7/1995 | Lavielle et al. | 546/206 |
| 5,792,796 | 8/1998 | Woodruff et al. | 514/561 |

FOREIGN PATENT DOCUMENTS

| | | | |
|---|---|---|---|
| 0 340 677 | 11/1989 | European Pat. Off. | |
| 0340677 | 11/1989 | European Pat. Off. | C07C 101/04 |
| 0414263 | 2/1991 | European Pat. Off. | C07C 229/28 |
| 0458751 | 11/1991 | European Pat. Off. | A61K 31/195 |
| 2543821 | 10/1975 | Germany | A61K 31/19 |
| 2626467 | 6/1976 | Germany | A61K 31/19 |
| 9114679 | 10/1991 | WIPO | C07D 235/02 |
| 9420500 | 9/1994 | WIPO | C07D 471/10 |

OTHER PUBLICATIONS

Silverman, The Organic Chemistry of Drug Design and Drug Action, pp. 15–21, 1992 no month provided.

Shimoyama et al., Spinal gabapentin ... test, Neuroscience Letters, vol. 222, Issue 1, pp. 65–67, Jan. 1997.

PCT International Search Report, PCT/US97/02295, May 1997.

Smith et al., "New Spiropiperidines as Potent and Selective Non–Peptide Tachykinin $NK_2$ Receptor Antagonists", *J. Med. Chem.*, 1995, vol. 38, No. 9, 3772–3779 no month provided.

Griffiths et al., "28. Novel Syntheses of Gabapentin via Addition of Hydrocyanic Acid to Cyclohexylidenemalonate or Cyano(cyclohexylidene)acetate", *Helvetica Chimica Acta*, 1991, vol. 74, 309–314 no month provided.

Suman–Chauhan et al., "Characterization of [$^3$H]gabapentin binding to a novel site in rat brain: homogenate binding studies", *European Journal of Pharmacology*, 1993, vol. 244, 293–301 no month provided.

Mellick and Seng, "The use of gabapentin in the treatment of reflex sympathetic dystrophy and a phobic disorder", *American Journal of Pain Management*, 1995, vol. 5, No. 1, 7–9 no month provided.

*Primary Examiner*—Johann Richter
*Assistant Examiner*—Rosalynd Keys
*Attorney, Agent, or Firm*—Elizabeth M. Anderson

[57] ABSTRACT

Substituted cyclic amino acids of formula

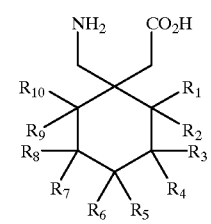

are disclosed and are useful as agents in the treatment of epilepsy, faintness attacks, hypokinesia, cranial disorders, neurodegenerative disorders, depression, anxiety, panic, pain, and neuropathological disorders. Processes for the preparation and intermediates useful in the preparation are also disclosed.

20 Claims, No Drawings

SUBSTITUTED CYCLIC AMINO ACIDS AS PHARMACEUTICAL AGENTS

This application claims the benefit of provisional U.S. patent application Ser. No. 60/013,432, filed Mar. 14, 1996.

BACKGROUND OF THE INVENTION

Compounds of formula

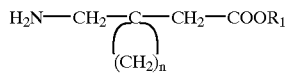

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The novel substituted cyclic amino acids, their derivatives, prodrugs, and pharmaceutically acceptable salts are useful in a variety of disorders. The disorders include: epilepsy, faintness attacks, hypokinesia, cranial disorders, neurodegenerative disorders, depression, anxiety, panic, pain, and neuropathological disorders.

The compounds are those of formula

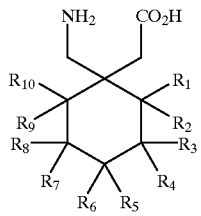

a pharmaceutically acceptable salt thereof or a prodrug thereof wherein $R_1$ to $R_{10}$ are each independently selected from straight or branched alkyl of from 1 to 6 carbon atoms, unsubstituted or substituted benzyl or phenyl which substituents are selected from halogen, alkoxy, alkyl, hydroxy, carboxy, carboalkoxy, trifluoromethyl, and nitro, and any $R_1$ to $R_{10}$, which is not one of the above, is hydrogen.
Especially preferred compounds of the invention are:
(1-aminomethyl-4-tert-butyl-cyclohexyl)-acetic acid;
(1-aminomethyl-3-methyl-cyclohexyl)-acetic acid;
(1-aminomethyl-3-methyl-cyclohexyl)-acetic acid [1R-(1α,3β)];
(1-aminomethyl-3-methyl-cyclohexyl)-acetic acid [1S-(1α,3β)];
cis (1-aminomethyl-4-methyl-cyclohexyl)-acetic acid;
cis (1-aminomethyl-4-isopropyl-cyclohexyl)-acetic acid;
(1-aminomethyl-2-methyl-cyclohexyl)-acetic acid;
(±)-(1-aminomethyl-3,3-dimethyl-cyclohexyl)-acetic acid;
(1-aminomethyl-3,3,5,5-tetramethyl-cyclohexyl)-acetic acid;
(1-aminomethyl-4-methyl-cyclohexyl)-acetic acid;
(1-aminomethyl-3-methyl-cyclohexyl)-acetic acid methyl ester monohydrochloride;
[1-(acetylamino-methyl)-3-methyl-cyclohexyl]-acetic acid; and
[2-(1-Aminomethyl-3-methyl-cyclohexyl)-acetylamino]-acetic acid monohydrochloride.

Novel intermediates useful in the preparation of the final products are disclosed as well as a novel process for the preparation of the compounds.

DETAILED DESCRIPTION

The compounds of the instant invention and their pharmaceutically acceptable salts are as defined by Formula I.

The term "alkyl" is a straight or branched group of from 1 to 6 carbon atoms including but not limited to methyl, ethyl, propyl, n-propyl, isopropyl, butyl, 2-butyl, tert-butyl, pentyl, hexyl, and n-hexyl.

Preferred groups are methyl and tert-butyl.

The benzyl and phenyl groups may be unsubstituted or substituted by from 1 to 3 substituents selected from halogen, alkyl, alkoxy, hydroxy, carboxy, carboalkoxy, trifluoromethyl, and nitro.

Halogen includes fluorine, bromine, chlorine, and iodine.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earit metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. For example, the compound of Example 1 is a mixture of all four possible stereoisomers. The compound of Example 6 is one of the isomers. The configuration of the cyclohexane ring carbon centers may be R or S in these compounds where a configuration can be defined.

The compounds of the invention may be synthesized, for example, by utilizing the general strategy (Scheme 1 below) outlined by Griffiths G., et al., *Helv. Chim. Acta*, 74:309 (1991). Alternatively, they may also be made as shown (in Scheme 2 below), analogously to the published procedure for the synthesis of 3-oxo-2,8-diazaspiro[4,5]decane-8-carboxylic acid tert-butyl ester (1) (Smith P. W., et al., *J. Med. Chem.*, 38:3772 (1995)). The compounds may also be synthesized by the methods outlined by Satzinger G., et al., (U.S. Pat. No. 4,024,175 and U.S. Pat. No. 4,152,326) (Schemes 3 and 4 below). The compounds may also be synthesized by the route outlined by Griffiths G., et al., *Helv. Chim. Acta*. 74:309 (1991) as in Scheme 5 below.

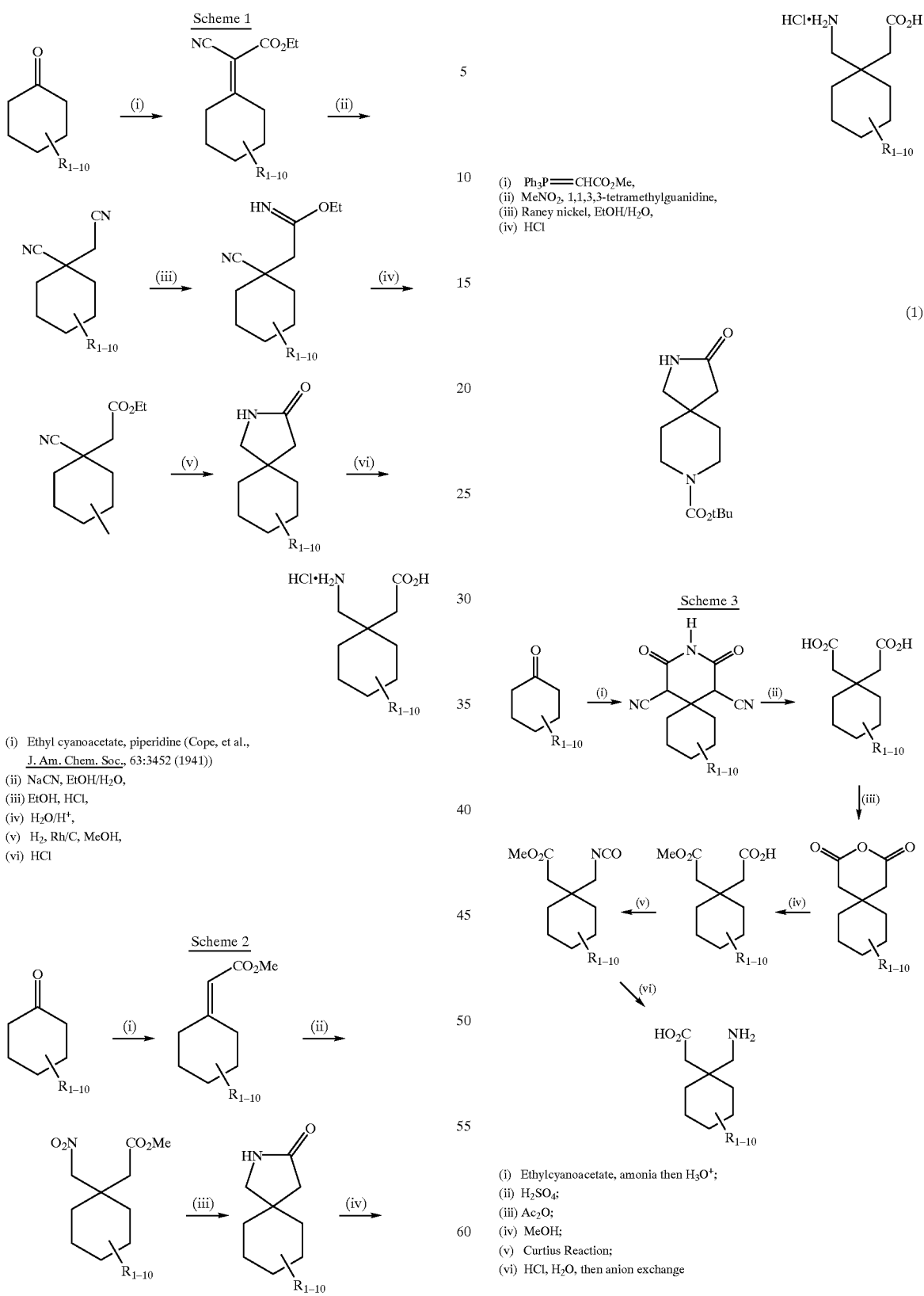

Scheme 4

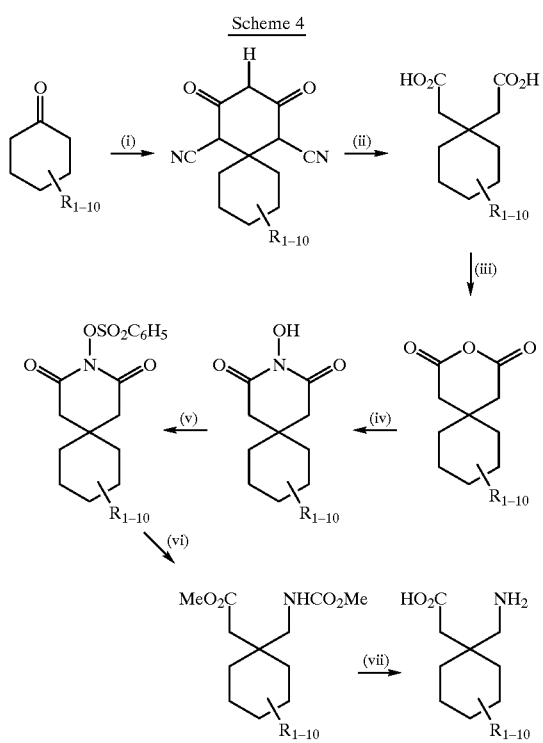

(i) Ethylcyanoacetate, ammonia then H₃O⁺;
(ii) H₂SO₄;
(iii) Ac₂O;
(iv) H₂NOH;
(v) PhSO₂Cl;
(vi) Et₃N, MeOH;
(vii) HCl, H₂O, then anion exchange

Scheme 5

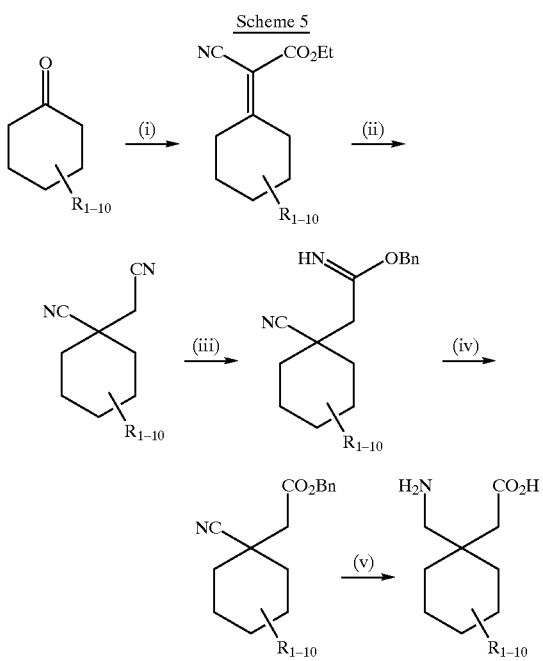

(i) Ethyl cyanoacetate, piperidine (Cope, et al., J. Am. Chem. Soc., 63:3452 (1941));
(ii) NaCN, EtOH/H₂O;
(iii) BnOH, HCl;
(iv) H₂O/H⁺;
(v) H₂, Rh/C, MeOH Examples of prodrugs are:

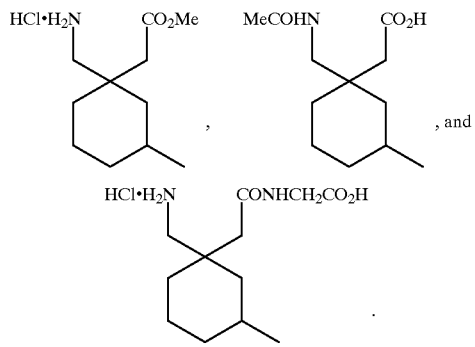

, and

These can be synthesized, for example, via the routes outlined in Schemes 6 through 8 below.

Scheme 6

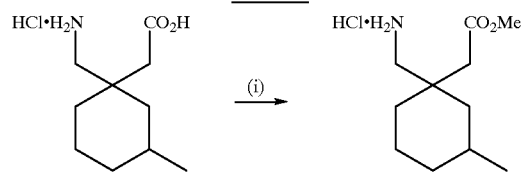

(i) MeOH, HCl reflux

Scheme 7

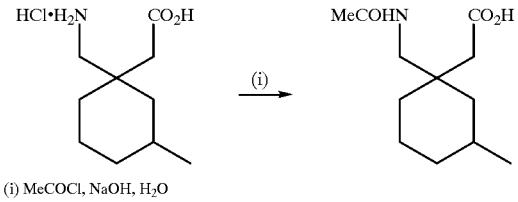

(i) MeCOCl, NaOH, H₂O

Scheme 8

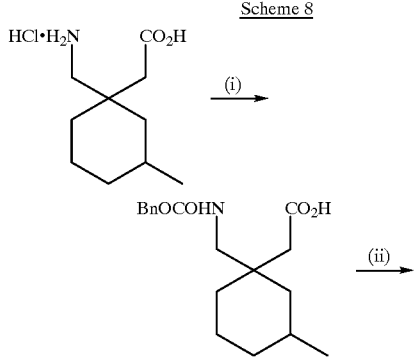

-continued

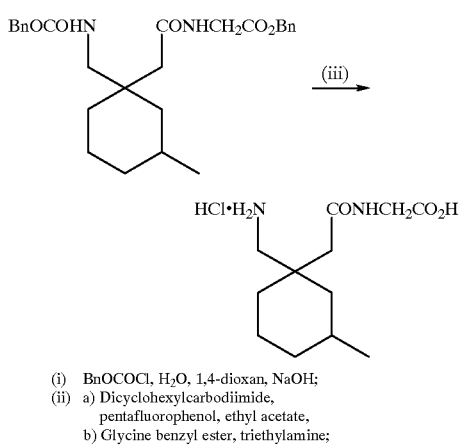

(i) BnOCOCl, H₂O, 1,4-dioxan, NaOH;
(ii) a) Dicyclohexylcarbodiimide, pentafluorophenol, ethyl acetate,
b) Glycine benzyl ester, triethylamine;
(iii) Pd(OH)₂/C, HCl, EtOH, H₂

The radioligand binding assay using [³H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel", Gee N., et al., *J. Diological Chemistry*, in press).

TABLE 1

| Compound | Structure | IC₅₀ (μM) |
| --- | --- | --- |
| (1-aminomethyl-4-tert-butyl-cyclohexyl)-acetic acid | 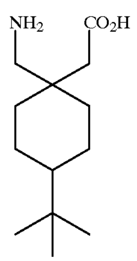 | 200 |
| (1-aminomethyl-3-methyl-cyclohexyl)-acetic acid | 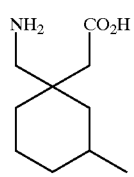 | 0.13 |
| (1-aminomethyl-3-methyl-cyclohexyl)-acetic acid [1R-(1α,3β)] | 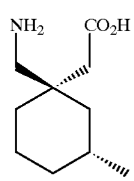 | 13 |
| (1-aminomethyl-3-methyl-cyclohexyl)-acetic acid [1S-(1α,3β)] | 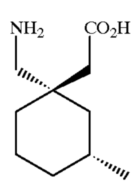 | .030 |

TABLE 1-continued

| Compound | Structure | IC₅₀ (μM) |
| --- | --- | --- |
| cis(1-aminomethyl-4-methyl-cyclohexyl)-acetic acid | 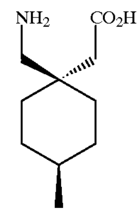 | 10 |
| cis(1-aminomethyl-4-isopropyl-cyclohexyl)-acetic acid | 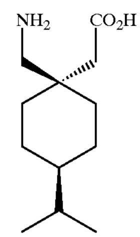 | 10 |
| (1-aminomethyl-2-methyl-cyclohexyl)-acetic acid | 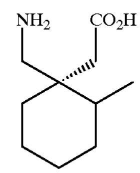 | 7 |
| (±)-(1-aminomethyl-3,3-dimethyl-cyclohexyl)-acetic acid | 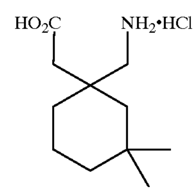 | 0.5 |
| (1-aminomethyl-3,3,5,5-tetramethyl-cyclohexyl)-acetic acid | 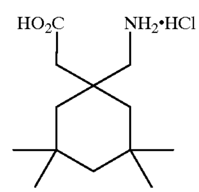 | 10 |
| (1-aminomethyl-4-methyl-cyclohexyl)-acetic acid | 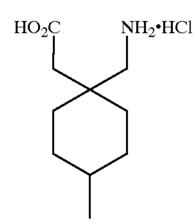 | 0.33 |

Table 1 above shows the binding affinity of the compounds of the invention to the $\alpha_2\delta$ subunit. Gabapentin (Neurontin®) is about 0.10 to 0.12 μM in this assay. The compounds of the instant invention are expected, therefore, to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)-cyclohexaneacetic acid of structural formula

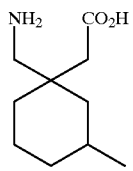

The compounds of the invention are also expected to be useful in the treatment of epilepsy. See Table 1 above for $IC_{50}$ data as compared to Neurontin®.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression.

Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS carrageenin-Induced Hyperalgesia

Nociceptive pressure thresholds were measured in the rat paw pressure test using an analgesymeter (Randall-Selitto method: Randall L. O. and Sellitto J. J., A method for measurement of analgesic activity on inflamed tissue. Arch. Int. Pharmacodyn., 4:409–419 (1957)). Male Sprague Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 μL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg, s.c.), morphine (3 mg/kg, s.c.) or saline at 3.5 hours after carageenin and nociceptive thresholds were examined at 4, 4.5, and 5 hours postcarrageenin.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light.

Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 28:901–905 (1989)).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 327:1–5 (1984)), was automated as previously described (Field, et al., Automation of the rat elevated X-maze test of anxiety. *Br. J. Pharmacol.*, 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 96(Suppl):312p (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out Sc at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signalled by chamber lights on and three 3-minute punished periods on fixed ratio 5 (by footshock concomitant to food delivery) signalled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 5:7–9 (1995)).

The compounds of the instant invention are also expected to be useful in treating the symptoms of manic, acute or chronic, single upside, or recurring. They are also expected to be useful in treating and/or preventing bipolar disorder (U.S. Pat. No. 5,510,381).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

EXAMPLE 1

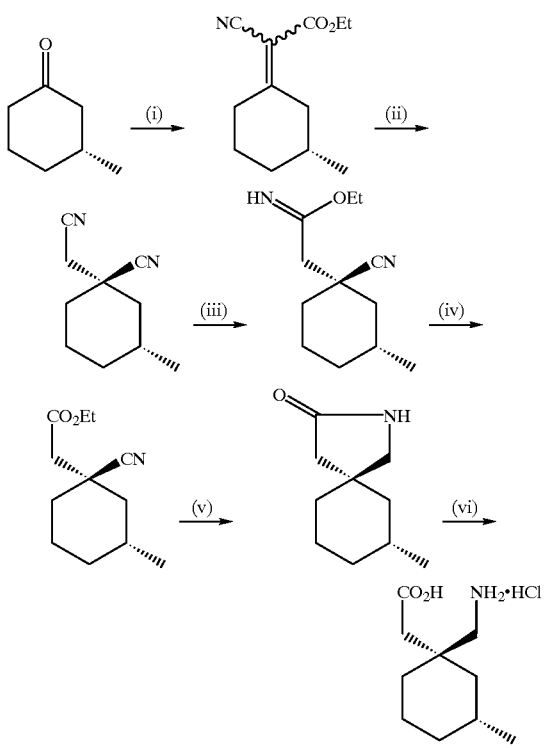

(i) EtO$_2$CCH$_2$CN, NH$_4$Ac, AcOH, Toluene, 120° C.
(ii) a. NaCN, EtOH (95%), H$_2$O, 115° C.; b. HCl (g)
(iii) EtOH, HCl (g), Toluene
(iv) HCl, H$_2$O
(v) H$_2$, EtOH/NH$_3$, Raney Nickel, 30–50° C.
(vii) HCl, H$_2$O, 140° C.

General Method, Exemplified by Synthesis of Trans (R)-3-ethyl Gabapentin

Step (i) Cyanoacetate

A mixture of 3-(R)-Methylcyclohexanone (125 mmol), ethyl cyanoacetate (124 mmol), ammonium acetate (12.5 mmol) and glacial acetic acid (24 mmol) were refluxed with a Dean Stark trap for 24 hours. The mixture was cooled and washed with H$_2$O. The H$_2$O washes were extracted with toluene. The toluene extracts were combined with the original organic layer, dried over MgSO$_4$, and the solvent evaporated. The crude oil was purified by Kugelrohr distillation to give an oil. Bpt oven temperature 150–160° C. Yield 86%.

$^1$H NMR (CDCl$_3$) 400 MHz: δ 1.01–1.05 (3H, m), 1.17–1.32 (1H, m), 1.35 (3H, t, J=7 Hz), 1.42–2.30 (6H, m), 2.98 (1H, d, J=13 Hz), 3.74 (1H, d, J=13 Hz), 4.27 (2H, q, J=7 Hz). MS (CI) m/z: 85, 91, 95, 135, 162, 178, 180, 200, 208 (100% MH$^+$), 209. IR (Film) υ$_{max}$ cm$^{-1}$: 3437, 2956, 2930, 2870, 2223, 1729, 1603, 1448, 1367, 1347, 1313, 1290, 1262, 1246, 1218, 1101, 1084, 1046, 1023, 974, 957, 914, 859, 822, 780.

| Microanalysis: | C$_{12}$H$_{17}$NO$_2$: |
|---|---|
| Calc: | C, 69.54; H, 8.27; N, 6.76. |
| Found: | C, 69.44; H, 8.22; N, 6.76. |

Step (ii) Bisnitrile

To a solution of NaCN (40 mmol) in 6 mL H$_2$O and 160 mL Ethanol (95%) was added the cyanoacetate (40 mmol). After 22 hours at reflux the cooled solution was filtered, the filtrate acidified with gaseous HCl, and filtered again. The solvent was removed, and the crude oil was purified by column chromatography to give a pale yellow crystalline solid. Yield 88% Mpt.

$^1$H NMR (CDCl$_3$) 400 MHz: δ 0.90 (1H, m), 0.98 (3H, d, J=6 Hz), 1.11 (1H, t, J=12 Hz), 1.38 (1H, dt, J=4.9 Hz), 160–190 (4H, m), 2.07 (2H, m), 2.68(2H, s). MS (CI) m/z: 91 (100%), 92, 108, 130, 136, 163, (50% MH$^+$), 180. IR (CH$_2$Cl$_2$) υ$_{max}$ cm$^{-1}$: 2956, 2932, 2862, 2234, 1714, 1457, 1447, 1427, 1386, 1358.

| Microanalysis: | C$_{10}$H$_{14}$N$_2$: |
|---|---|
| Calc: | C, 74.04; H, 8.70; N, 17.27. |
| Found: | C, 74.05; H, 8.71; N, 17.25. |

Step (iii) Imidate

To a solution of the binitrile (6.2 mmol) in 30 mL ethanol (absolute) was added 30 mL dried toluene. The solution was chilled in ice while saturating with gaseous HCl. The stoppered solution was then left to stand at room temperature for 24 hours. The solvent was removed, and the solid residue was triturated with diethyl ether to obtain a ppt which was dried to give a white crystalline solid. Yield 50%. Mpt 118–120° C.

$^1$H NMR (DMSO) 400 MHz: δ 0.8–0.89 (1H, m), 0.91 (3H, d, J=6.3 Hz), 1.06–1.12 (1H, m), 1.24–1.35 (1H, m), 1.37 (3H, t, J=7 Hz), 1.41–1.95 (6H, mn), 3.02 (2H, s), 4.49 (2H, q, J=7 Hz). MS (CI) m/z: 91, 133, 154, 164, 179, 181, (100% MH$^+$-CN), 195 (MH$^+$), 209. IR (CH$_2$Cl$_2$) υ$_{max}$ cm$^{-1}$: 2957, 2938, 2858, 2233, 1651, 1573, 1446, 1388, 1361, 1137, 1103, 1022, 1005, 952, 933, 874, 834.

| Microanalysis: | $C_{12}H_{20}N_2O.1.08$ HCl: |
|---|---|
| Calc: | C, 58.19; H, 8.58; N, 11.31. |
| Found: | C, 58.25; H, 8.59; N, 11.59. |

Step (iv) Ester

The imidate (1.1 mmol) was dissolved in ice cold $H_2O$ (40 mL) and the pH adjusted with 1N HCl to pH 1.5. The solution was stirred at room temperature for hours. Ethylacetate was added (30 mL), and the organic layer was washed with $H_2O$, dried, and the solvent removed to leave a clear oil. Yield 82%.

$^1$H NMR (CDCl$_3$) 400 MHz: δ 0.78–0.90 (1H, m), 0.93 (3H, d, J=6 Hz), 0.97–1.00 (1H, m), 1.23–1.25 (1H, m), 1.29 (3H, t, J=7.2 Hz), 1.59–1.80 (4H, m), 2.05–2.08 (2H, Br t), 2.54 (2H, s), 4.20 (2H, q, J=7.2 Hz). MS (CI) m/z: 88, 95, 109, 122, 137, 160, 164 (100% M$^+$-EtOH), 182, 183, 199, 210 (60% MH$^+$), 230. IR (Film) $\upsilon_{max}$ cm$^{-1}$: 2930, 2870, 2235, 1737, 1458, 1414, 1375, 1345, 1264, 1196, 1171, 1096, 1041, 1026, 959, 847.

| Microanalysis: | $C_{12}H_{19}NO_2$: |
|---|---|
| Calc: | C, 68.87; H, 9.15; N, 6.69. |
| Found: | C, 68.87; H, 9.11; N, 6.90. |

Step (v) Lactam

The ester (8.9 mmol) was dissolved in NH$_3$/EtOH (7%, 40 mL) along with prewashed Raney Nickel (H$_2$O followed by EtOH) in a 250 mL Parr flask. The solution was hydrogenated at 30° C., 46 psi for 24 hours. The cooled solution was filtered through a pad of celite, washing with ethylacetate. The solvent was removed from the filtrate to leave a white solid. Yield 30%. Mpt 92–98° C.

$^1$H NMR (DMSO) 400 MHz: δ 0.75–0.82 (1H, m), 0.84 (3H, d, J=6.4 Hz), 0.88–0.94 (1H, m), 1.14–1.19 (1H, m), 1.20–1.50 (2H, m), 1.50–1.63 (4H, m), 1.91 (2H, s), 3.03 (2H, s), 7.42 (1H, s). MS (CI) m/z: 166, 167, 168 (100% MH$^+$), 182, 196. IR (Film) $\upsilon_{max}$ cm$^{-1}$: 3260, 2907, 1695, 1652, 1446, 1318, 1255, 1210, 1068.

| Microanalysis: | $C_{10}H_{17}NO$: |
|---|---|
| Calc: | C, 71.81; H, 10.25; N, 8.37. |
| Found: | C, 71.80; H, 10.29; N, 8.31. |

Step (vi) 3-Methyl Gabapentin

The lactam (2.17 mmol) was dissolved in a solution of 10 M HCl (5 mL) and $H_2O$ (5 mL), and the mixture was refluxed at approximately 140° C. for 5 hours. The cooled solution was diluted with 10 mL $H_2O$ and 10 mL DCM and the aqueous layer was further washed with 2×15 mL DCM. The aqueous layer was then reduced to dryness to leave a white solid. Yield 76%. Mpt 148–155° C. [α]$_D$=−2.5 (T-20° C., c=1, MeOH). One isomer (RR).

$^1$H NMR (CDCl$_3$) 400 MHz: δ 06.9–0.79 (1H, m), 0.82 (3H, d, J=6 Hz), 0.87–0.90 (1H, m), 1.12–1.20 (1H, dt, J=4.5, 13.3 Hz), 1.34–1.50 (3H, m), 1.60–1.63 (3H, m), 2.30 (2H, s), 3.01 (2H, s), 7.93 (3H, Br s). MS (CI) m/z: 95, 109, 121, 151, 167, 168 (100% MH$^+$-H$_2$O), 186 (MH$^+$). IR (MeOH) $\upsilon_{max}$ cm$^{-1}$: 2924, 2353, 1708, 1599, 1523, 1454, 1216.

| Microanalysis: | $C_{10}H_{19}NO_2.1.1$ HCl: |
|---|---|
| Calc: | C, 53.29; H, 8.99; N, 6.21. |
| Found: | C, 53.23; H, 8.99; N, 6.45. |

EXAMPLE 2

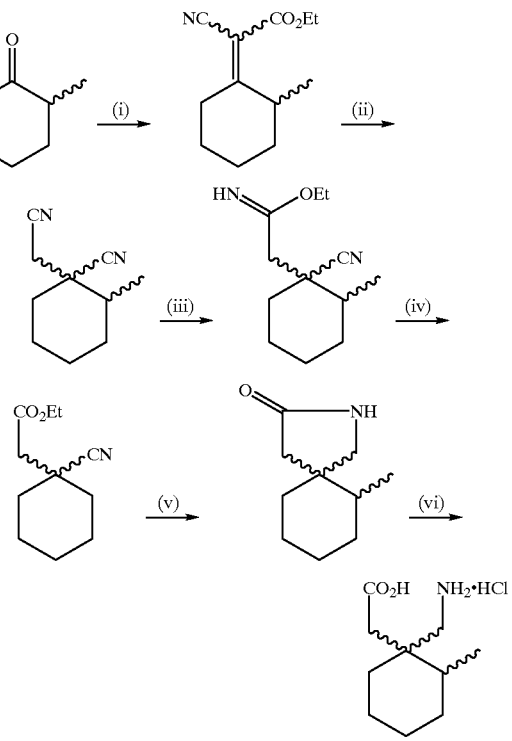

(i) EtO$_2$CCH$_2$CN, NH$_4$Ac, AcOH, toluene, 120° C.;
(ii) a. NaCN, EtOH (95%), H$_2$O, 115° C.; b. HCl (g);
(iii) EtOH, HCl (g), toluene;
(iv) HCl, H$_2$O;
(v) H$_2$, EtOH/NH$_3$, Raney Nickel, 30–50° C.;
(vi) HCl, H$_2$O, 140° C.

Cis/trans (RS)-2-methyl Gabapentin

Step (i) Cyanoacetate (±)-2-Methylcyclohexanone (80 mmol), ethyl cyanoacetate (80 mmol), ammonium acetate (8 mmol), and glacial acetic acid (16 mmol) were reacted as in the general method Step (i), to give a clear oil. Yield 76%. Bpt oven temperature 120–140° C., 3 mbar.

$^1$H NMR (CDCl$_3$) 400 MHz: δ 1.23 (3H, dd, J=7, 10 Hz), 1.35 (3H, t, J=7 Hz), 1.55–1.82 (5H, m), 1.93–2.05 (1H, m), 2.17 (1H, dt, J=5, 14 Hz), 2.47 (1H, dt, J=5, 9 Hz), 2.92–2.97 (1H, Br d, J=15 Hz), 3.30–3.35 (1H, m), 3.81–3.86 (1H, Br d, J=15 Hz), 4.06–4.14 (1H, m), 4.23–4.30 (3H, dq, J=1, 6 Hz). MS (CI) m/z: 91, 105, 120, 162, 180, 184, 189, 208 (MH$^+$), 216, 233, 234, 242, 261, 262 (100%), 263. IR (Film) $\upsilon_{max}$ cm$^{-1}$: 3438, 2978, 2938, 2864, 2223, 1732, 1596, 1463, 1447, 1391, 1368, 1334, 1311, 1289, 1247, 1224, 1164, 1144, 1103, 1077, 1058, 1032, 993, 982, 957, 907, 892, 858, 781.

| Microanalysis: | $C_{12}H_{17}NO_2$: |
|---|---|
| Calc: | C, 69.54; H, 8.27; N, 6.76. |
| Found: | C, 69.26; H, 8.26; N, 6.66. |

Step (ii) Bisnitrile

The cyanoacetate (37 mmol) and NaCN (37 imol) were reacted as in the general method Step (ii). The crude solid was purified by column chromatography (3:1, heptane:ethylacetate) to give a clear oil. Yield 76%.

$^1$H NMR (CDCl$_3$) 400 MHz: δ 1.06 (3H, d, J=6.8 Hz), 1.11 (3H, d, J=6.8 Hz), 1.20–2.20, (18 H, m), 2.77 (2H, dd, J=16.8 Hz), 2.63 (2H, dd, J=16.8 Hz). MS (CI) m/z: 91, 95, 108, 109, 136, 16.3 (100% MH$^+$). IR (Film) $\upsilon_{max}$ cm$^{-1}$: 2939, 2865, 2255, 2237, 1750, 1720, 1450, 1425, 1387, 1356, 1337, 1316, 1269, 1160, 1097, 992, 929, 879.

| Microanalysis: | $C_{10}H_{14}N_2$.0.1 $H_2O$: |
|---|---|
| Calc: | C, 73.49; H, 8.69; N, 16.86. |
| Found: | C, 73.24; H, 8.73; N, 17.08. |

Step (iii) Imidate

The binitrile (7.3 imol) was reacted as in the general method Step (iii) to give a white solid. Yield 70%. Mpt 107–114° C.

$^1$H NMR (DMSO) 400 MHz: δ 1.00–1.06 (3H, 2xt, J=6.4 Hz), 1.10–1.38 (2H, m), 1.38 (3H, t, J=6.8 Hz), 1.40–2.10 (7H, m), 2.86, 2.92, 3.10, 3.28 (2H, 4xd, J=14, 14.4, 14.8, 14 Hz, respectively), 4.48 (2H, q, J=6.8 Hz). MS (CI) m/z: 87, 95, 154, 163, 1.81, 195, 209 (100% MH$^+$), 210. IR (CH$_2$Cl$_2$) $\upsilon_{max}$ cm$^{-1}$: 2938, 2864, 2664, 2235, 1656, 1575, 1446, 1389, 1367, 1139, 1100, 1007, 948, 881, 837, 809.

| Microanalysis: | $C_{12}H_{20}N_2O$.1.06 HCl: |
|---|---|
| Calc: | C, 58.37; H, 8.60; N, 11.34. |
| Found: | C, 58.15; H, 8.63; N, 11.60. |

Step (iv) Ester

The imidate (4.1 mmol) was reacted as in the general method Step (iv) to give a clear oil. Yield 82%.

$^1$H NMR (CDCl$_3$) 400 MHz: δ 1.03, 1.09 (3H, 2xd, J=7 Hz), 1.27–1.30 (3H, m), 1.32–2.00 (8H, m), 2.10–2.20 (1H, m), 244, 2.82 (3H, 2xd, J=14.8 Hz), 2.54 (1H, m), 4.16–4.22 (2H, m). MS (CI) m/z: 88, 95, 109, 122, 164, 182, 210 (MH$^+$ 100%). IR (Film) $\upsilon_{max}$ cm$^{-1}$: 2936, 2864, 2234, 1737, 1449, 1418, 1385, 1372, 1345, 1270, 1225, 1186, 1128, 1098, 1029, 1001, 932, 883, 864, 808, 732.

| Microanalysis: | $C_{12}H_{19}NO_2$: |
|---|---|
| Calc: | C, 68.87; H, 9.15; N, 6.69. |
| Found: | C, 68.84; H, 9.13; N, 6.75. |

Step (v) Lactam

The ester (8.4 mmol) was reacted as in the general method Step (v) for 24 hours at 10° C., 50 psi. The crude oil was purified by column chromatography (ethylacetate), to give a white solid. Yield 34%. Mpt 85–90° C.

$^1$H NMR (CDCl$_3$) 400 MHz: δ 0.88–0.91 (3H, dd, J=4, 6.8 Hz), 1.41–1.78 (9H, m), 2.00–2.30 (2H, m) 3.06–3.23 (2H, m), 7.27 (1H, Br s). MS (CI) m/z: 81, 95, 108, 137, 166, 167, 168 (100 MH$^+$), 169, 182, 196. IR (CH$_2$cl$_2$) $\upsilon_{max}$ cm$^{-1}$: 3210, 2920, 2846, 1690, 1491, 1446, 1379, 1298, 1242, 1070.

| Microanalysis: | $C_{10}H_{17}NO$: |
|---|---|
| Calc: | C, 71.81; H, 10.24; N, 8.37. |
| Found: | C, 71.83; H, 10.19; N, 8.27. |

Step (vi) 2-Methyl Gabapentin

The lactam (2.5 mmol) was reacted as in the general method Step (vi) to give a white solid. Yield 42%. Mpt 108–110° C. [α]$_D$=0 (T=20.5° C., C=1, MeOH). Two diastereomers 3:1.

$^1$H NMR (DMSO +D$_2$O) 400 MHz: δ 0.79, 0.85 (3H, 2xd, J=6.8 Hz), 1.21–1.65 (9H, m), 2.22, 2.43 (1H, 2xd, J=15 Hz), 2.46, 2.49 (1H, 2xd, J=15 Hz), 2.83–2.92 (1H, 2xd, J=13.6 Hz), 3.05, 3.15 (1H, 2xd, J=13.6 Hz). MS (CI) m/z: 95, 109, 137, 166, 168 (100% lactam), 169 (MH$^+$-H$_2$O), 186 (MH+), 196. IR (MeOH) $\upsilon_{max}$ cm$^{-1}$: 3384, 2931, 2861, 1703, 1608, 1506, 1456, 1406, 1232, 1206, 1068, 999.

| Microanalysis: | $C_{10}H_{19}NO_2$.1.3 HCl. |
|---|---|
| Calc: | C, 51.64; H, 8.79; N, 6.02. |
| Found: | C, 51.66; H, 8.91; N, 6.16. |

EXAMPLE 3

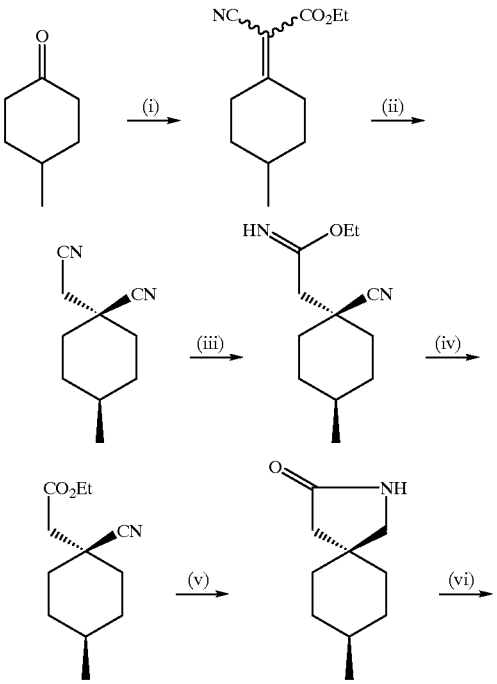

-continued

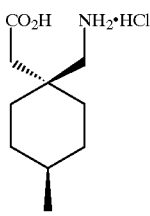

(i) EtO₂CCH₂CN, NH₄Ac, AcOH, toluene, 120° C.;
(ii) a. NaCN, EtOH (95%), H₂O, 115° C.; b. HCl (g);
(iii) EtOH, HCl (g), toluene;
(iv) HCl, H₂O;
(v) H₂, EtOH/NH₃, Raney Nickel, 30–50° C.;
(vi) HCl, H₂O, 140° C.;

Step (i) Cyanoacetate

The 4-Methylcyclohexanone (125 mmol), ethyl cyanoacetate (124 mmol), ammonium acetate (12.4 mmol), and glacial acetic acid (24.4 mmol) were reacted as in the general method Step (i) for 8 hours to give a clear oil. Yield 82%. Bpt oven temperature 160–190° C., 4 mbar.

$^1$H NMR (CDCl$_3$) 400 MHz: δ 0.95 (3H, d, J=6.8 Hz), 1.20–1.31 (2H, m), 1.35 (3H, t, J=7.2 Hz), 1.80–1.90 (1H, m), 1.90–2.10 (2H, m), 2.15 (1H, dt, J=4.8, 13.6 Hz), 2.34 (1H, dt, J=4.8, 13.6 Hz), 3.02 (1H, dd, J=2.4, 14 Hz), 3.84 (1H, dd, J=2.4, 14 Hz), 4.27 (2H, q, J=7.2 Hz). MS (CI) m/z: 114, 134, 151, 162, 179, 180, 207, 208 (100% MH$^+$), 209, 236. IR (Film) υ$_{max}$ cm$^{-1}$: 2927, 2225, 1728, 1601, 1456, 1367, 1288, 1242, 1192, 1095, 1028, 959, 857, 779.

| Microanalysis: | C₁₂H₁₇NO₂: |
|---|---|
| Calc: | C, 69.54; H, 8.27; N, 6.76. |
| Found: | C, 69.39; H, 8.27; N, 6.77. |

Step (ii) Binitrile

The cyanoacetate (30 mmol) and NaCN (30 mmol) were reacted as in the general method Step (ii) to give a crude oil. The oil was purified by column chromatography (3:1, heptane:ethylacetate) to give a clear oil. Yield 66%.

$^1$H NMR (CDCl$_3$) 400 MHz: δ 0.98 (3H, d, J=5.6 Hz), 1.30–1.40 (3H, m), 1.50 (2H, m), 1.73–1.92 (2H, m), 2.10 (2H, d, J=12.4 Hz), 2.68 (2H, s). MS (CI) m/z: 95, 136, 163 (100% MH$^+$), 164, 182. IR (Film) υ$_{max}$ cm$^{-1}$: 3628, 3288, 2932, 2859, 2252, 2238, 1779, 1748, 1721, 1626, 1455, 1423, 1381, 1371, 1332, 1287, 1263, 1194, 1170, 1143, 1109, 1004, 953, 893, 852.

| Microanalysis: | C₁₀H₁₄N₂.0.6 H₂O: |
|---|---|
| Calc: | C, 72.74; H, 8.74; N, 16.97. |
| Found: | C, 72.98; H, 8.61; N, 16.65. |

Step (iii) Imidate

The binitrile (12.4 mmol) was reacted as in the general method Step (i) to give a slightly impure white solid. No purification was attempted, and solid was used in next step.

Step (iv) Ester

The imidate (4.7 mmol) was reacted as in the general method Step (iv) to give a low melting solid. Yield 75%, based on binitrile.

$^1$H-NMR (CDCl$_3$) 400 MHz: δ 0.92–1.01 (3H, m), 1.27–1.31 (3H, m), 1.37 (5H, m), 1.70–1.73 (2H, m), 2.10–2.13 (2H, m), 2.54 (2H, s), 4.21 (2H, q, J=7.2 Hz). MS (CI) m/z: 95, 112, 122, 164, 182 (100% MH$^+$-C$_2$H$_5$), 210 (MH$^+$). IR (CH$_2$Cl$_2$) υ$_{max}$ cm$^{-1}$: 2926, 2856, 2235, 1735, 1733, 1452, 1373, 1345, 1253, 1191, 1033, 953.

| Microanalysis: | C₁₂H₁₉N₂O₂.0.12 H₂O: |
|---|---|
| Calc: | C, 68.16; H, 9.17; N, 6.62. |
| Found: | C, 68.14; H, 8.91; N, 6.77. |

Step (v) Lactam

The ester (2.9 mmol) was reacted as in the general method Step (v) to give a white fibrous solid. Yield 95%. Mpt 150–152° C.

$^1$H NMR (DMSO) 400 MHz: δ 0.86 (3H, d, J=6 Hz), 0.93–1.06 (2H, m), 1.27–1.30 (3H, m), 1.51 (2H, d, J=11.6 Hz), 1.62 (2H, d, J=13.2 Hz), 1.92 (2H, s), 3.02 (2H, s), 7.43 (1H, Br s). MS (CI) m/z: 81, 95, 110, 166, 167, 168 (100% MH$^+$), 169, 182, 196. IR (CH$_2$Cl$_2$) υ$_{max}$ cm$^{-1}$: 3189, 3093, 2945, 2921, 2864, 1679, 1486, 1447, 1417, 1260.

| Microanalysis: | C₁₀H₁₇NO.0.15 H₂O: |
|---|---|
| Calc: | C, 70.67; H, 10.17; N, 8.24. |
| Found: | C, 70.69; H, 10.05; N, 7.87. |

Step (vi) 4-Methyl Gabapentin

The lactam (2.5 mmol) was reacted as in the general method Step (vi) to give an off-white hygroscopic solid. Yield 92%. Mpt 146–151° C. [α]$_D$=0 (T=21° C., C=1, MeOH). One diastereomer (cis).

$^1$H NMR (DMSO) 400 MHz: δ 0.88 (3H, d, J=6 Hz), 1.02–1.12 (2H, m), 1.25–1.32 (3H, m), 143–1.47 (2H, m), 2.33 (2H, s), 2.99 (2H, s), 8.03 (3H, Br s), 12.33 (1H, Br S). MS (CI) m/z: 81, 95, 109, 166, 167, 168 (100% MH$^+$-H$_2$O), 169, 182, 186 (MH$^+$), 196. IR (MeOH) υ$_{max}$ cm$^{-1}$: 3393, 2925, 2862, 1714, 1613, 1514, 1451, 1387, 1251, 1232, 1192, 1151, 1119, 864.

| Microanalysis: | C₁₀H₁₉NO₂.1 HCl.1 H₂O: |
|---|---|
| Calc: | C, 50.04; H, 9.26; N, 5.84. |
| Found: | C, 50.04; H, 9.18; N, 5.82. |

EXAMPLE 4

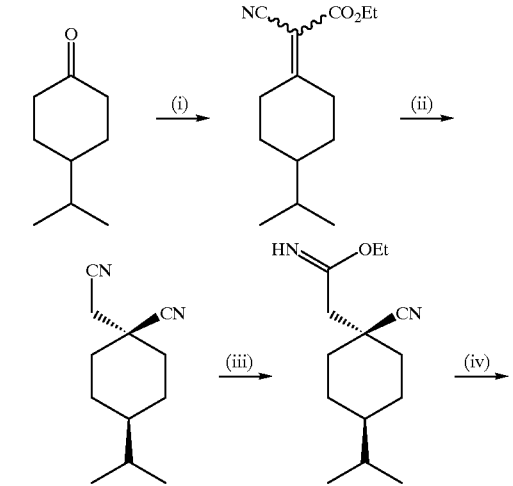

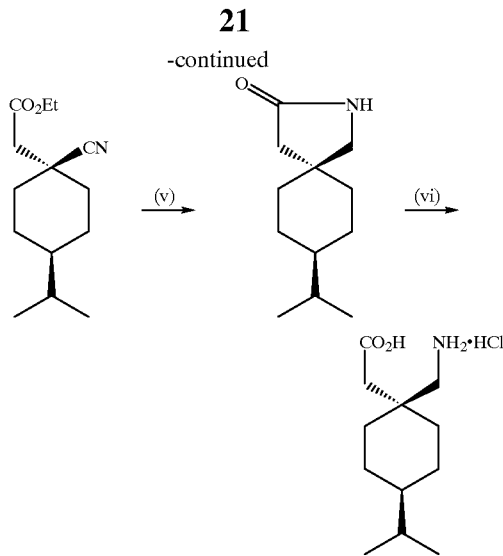

(i) EtO₂CCH₂CN, NH₄Ac, AcOH, toluene, 120° C.;
(ii) a. NaCN, EtOH (95%), H₂O, 115° C.; b. HCl (g);
(iii) EtOH, HCl (g), toluene;
(iv) HCl, H₂O;
(v) H₂, EtOH/NH₃, Raney Nickel, 30–50° C.;
(vi) HCl, H₂O, 140° C.;

Cis 4-isopropyl Gabapentin

Step (i) Cyanoacetate

The 4-Isopropyl-cyclohexanone (57 mmol), ethylacetate (57 mmol), ammoninm acetate (58 mmol), and glacial acetic acid (11.3 mmol) were reacted as in the general method Step (i). Kugelrohr distillation gave a clear oil. Yield 83%. Bpt oven temperature 170–19° C., 4 mbar.

¹H NMR (CDCl₃) 400 MHz: δ 0.89 (6H, d, J=6.8 Hz), 1.20–1.33 (2H, m), 1.35 (3 H, t, J=7.2 Hz), 1.37–1.50 (2H, m), 2.00–2.11 (3H, m), 2.30 (1H, dt, J=5, 14 Hz), 3.10 (1H, m), 3.92 (1H, m), 4.27 (2H, q, J=7.2 Hz). MS (CI) m/z: 163, 179, 190, 207, 208, 235, 236 (100% MH⁺), 237, 264. IR (Film) $\upsilon_{max}$ cm⁻¹: 2959, 2871, 2225, 1730, 1603, 1448, 1387, 1368, 1291, 1264, 1239, 1214, 1190, 1140, 1101, 1029, 918, 852, 777.

| Microanalysis: | C₁₄H₂₁NO₂: |
|---|---|
| Calc: | C, 71.46; H, 8.99; N; 5.95. |
| Found: | C, 71.28; H, 8.95; N, 5 90. |

Step (ii) Binitrile

The cyanoacetate (37 mmol) and NaCN (37 mmol) were reacted as in the general method Step (ii) to give a yellow solid. Yield 100%. Mpt 79–81° C.

¹H NMR (CDCl₃) 400 MHz: δ 0.91 (6H, d, J=6.8 Hz), 1.00–1.20 (1H, m), 1.3–1.6 (5H, m), 1.85 (2H, d, J=12.8 Hz), 2.14 (2H, d, J=12 Hz), 2.70 (2H, m). MS (CI) m/z: 95, 121, 148, 164, 191 (100% MH⁺), 192, 209, 210, 219, 231. IR (CH₂Cl₂) $\upsilon_{max}$ cm⁻¹: 2961, 2933, 2868, 2250, 2237, 1468, 1451, 1388, 1370, 1344, 1318, 1266, 1238, 1216, 1146, 1093, 1065, 1035; 998, 966, 934, 909, 738.

| Microanalysis: | C₁₂H₁₈N2: |
|---|---|
| Calc: | C, 75.74; H, 9.53; N, 14.72. |
| Found: | C, 75.45; H, 9.51; N, 14.64. |

Step (iii) Imidate

The binitrile (12.3 mmol) was reacted as in the general method Step (iii) to give a slightly impure white solid. No purification was attempted and solid was used in next step.

Step (iv) Ester

The imidate (4.4 mmol) was reacted as in the general method Step (iv) to leave a low melting solid. Yield 76% based on binitrile.

¹H NMR (CDCl₃) 400 MHz: δ 0.89 (6H, d, J=6.8 Hz), 0.91–1.04 (1H, m), 1.29 (3H, t, J=7 Hz), 1.33–1.51 (5H, m), 1.74–1.78 (2H, m), 2.14–2.17 (2H, m), 2.54 (2H,5), 4.17–4.22 (2H, q, J=7 Hz). MS (CI) m/z: 88, 123, 150, 192 (MH⁺-EtOH), 210 (MH⁺-CO), 238 (100% MH⁺). IR (Film) $\upsilon_{max}$ cm⁻¹: 2955, 2927, 2863, 2235, 1733, 1450. 1369, 1244, 1187, 1030, 933.

| Microanalysis: | C₁₄H₂₃NO₂.0.12 H₂O: |
|---|---|
| Calc: | C, 70.21; H, 9.78; N, 5.85. |
| Found: | C, 70.18; H, 9.82; N, 6.03. |

Step (v) Lactam

The ester (2.9 mmol) was hydrogenated as in the general method Step (v) at 50° C., 50 psi, to give a crude solid. The solid was purified by column chromatography to give a white solid. Yield 38%. Mpt 130–134° C.

¹H NMR (CDCl₃) 400 MHz: δ 0.85–0.90 (6H, dd, J=0.8, 6.8 Hz), 1.00–1.05 (3H, m), 1.34–1.45 (3H, m), 1.63–1.65 (2H, m), 1.73–1.81 (2H, m), 2.13 (2H, d, J=0.8 Hz), 3.19 (2H, s), 5.91 (1H, Br s). MS (CI) m/z: 95, 152, 194, 195, 196 (100% MH⁺), 197, 210, 224. IR (CH₂Cl₂) $\upsilon_{max}$ cm⁻¹: 3210, 3094, 2931, 2857, 1699, 1493, 1449, 1382, 1322, 1301, 1265, 919, 788.

| Microanalysis: | C₁₂H₂₁NO: |
|---|---|
| Calc: | C, 73.80; H, 10.84; N, 7.77. |
| Found: | C, 73.83; H, 10.90; N, 7.11. |

Step (vi) 4-isopropyl Gabapentin

The lactam (1 mmol) was reacted as in the general method Step (vi) to give a white powder. Yield 60%. Mpt 167–170° C. [α]$_D$=0 (T=20° C., C=1, MeOH). One diastereomer (cis).

¹H NMR (DMSO) 400 MHz: δ 0.84 (6H, d, J=6.8 Hz), 0.90–1.00 (1H, m), 1.00–1.56 (2H, m), 1.23–1.30 (2H, m), 1.38–1.48 (3H, m), 1.66–1.70 (2H, m), 2.32 (2H, s), 2.97 (2H, s), 8.00 (3H, Br s), 12.00 (1H, Br s). MS (CI) m/z: 190, 196 (100% lactam H⁺), 214 (MH⁺). IR (MeOH) $\upsilon_{max}$ cm⁻¹: 3557, 3144, 3027, 2949, 2865, 2354, 1712, 1591, 1507, 1455, 1468, 1409, 1322, 1286, 1246, 1199, 1077, 852.

| Microanalysis: | C₁₂H₂₃NO₂.1.12 HCl: |
|---|---|
| Calc: | C, 56.71; H, 9.57; N, 5.51. |
| Found: | C, 56.77; H, 9.56; N, 5.51. |

EXAMPLE 5

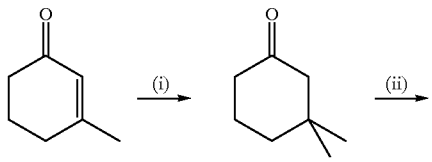

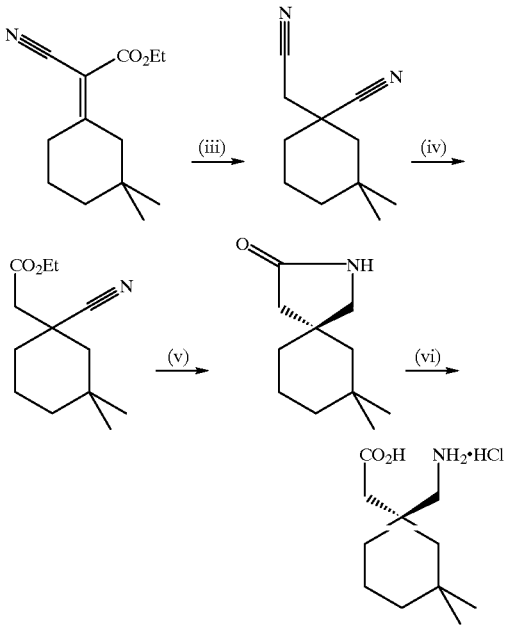

(i) CuL, MeLi, NH4Cl, NH3 (92%);
(ii) NCCH2CO2Et, NH4OAc, AcOH, toluene (83%);
(iii) NaCN, EtOH, H2O (57%);
(iv) HCl, EtOH, toluene (93%);
(v) H2, Raney Nickel, EtOH, NH3 (84%);
(vi) HCl, H2O, (64%);

Step (i) 3,3-Dimethyl-cyclohexanone

Synthesised via the method outlined by Pelletier S. W. and Mody N. V., *J. Org. Chem.*, 41:1069 (1969).

A solution of lithium dimethyl cuprate was prepared by the addition of methyl lithium (1.4 M in ether, 77.25 mL, 2.45 mol) to copper (I) iodide (8.8 g, 0.046 mol) under argon. The solution was cooled to 0° C., and 3-methyl-cyclohexen-1-one (5 mL, 0.044 mol) was added dropwise, with stirring, and a deep yellow precipitate was formed.

The suspension was stirred at room temperature for 1 hour before being poured into a solution of aqueous ammonia (100 mL) and ammonium acetate (ca. 5 g). The layers were separated and the aqueous layer was washed with diethyl ether (3×50 mL). The combined organics were washed with saturated brine (3×100 mL), dried (Mgso4), and the solvent removed in vacuo to leave a dark yellow liquid.

$^1$H NMR (CDCl$_3$) 400 MHz: 0.98 (6H, s, 2×Me), 1.59 (2H, m), 1.88 (2H, m), 2.14 (2H, m), 2.26 (2H, m). IR (Film) $\upsilon_{max}$ cm$^{-1}$: 2956, 1711 (C=O), 1457, 1368, 1292, 1226, 1076.

Step (ii) Cyanoacetate

To a solution of 3,3-dimethyl-cyclohexanone (4 g, 0.032 mol) in toluene (25 mL) was added ethyl cyanoacetate (3.37 mL, 0.032 mol, 1 eq.), ammonium acetate (0.24 g, 0.003 mol, 0.1 eq.), and acetic acid (0.36 mL, 0.006 mol, 0.2 eq.). The yellow solution was heated to reflux while attached to a Dean-Stark trap, and heating was continued until no more water condensed in the trap. After cooling, the now orange solution was washed with water (3×2.5 mL) and the organic layer dried (MgSO$^4$). Filtration and removal of the solvent in vacuo gave the crude product as a deep orange liquid. Purification was achieved by Kugelrohr distillation to leave the mixture of cis and trans products as a pale yellow liquid, bp 160–170° C., 4 mbar (5.83 g, 83%).

$^1$H NMR (CDCl$_3$) 400 MHz: 0.96 (6H, s, 2×Me), 0.99 (6H, S, 2×Me), 1.34 (6H, m, 2×Me of ester), 1.49 (4H, m), 1.75 (2H, quin, J=6.4), 1.82 (2H, quin, J=6.4), 2.46 (2H, s), 2.60 (2H, t, J=6.4), 2.80 (2H, s) 2.93 (2H, t, J=6.4), 4.27 (4H, m, 2×CH2 ester). MS (CI) z/e: 222 (M$^+$=1, 100%), 221 (5), 206 (4), 194 (6), 176 (5). IR (Film) $\upsilon_{max}$ cm$^{-1}$: 2958, 2870, 2224 (CN), 1731 (C=O), 1606 (C=C), 1277, 1223.

| Microanalysis: | C$_{13}$H$_{19}$O$_2$N: |
|---|---|
| Calc: | C, 70.56; H, 8.65; N, 6.32. |
| Found: | C, 70.35; H, 8.79; N, 6.25. |

Step (iii) Bisnitrile

To a solution of the unsaturated cyanoester (1.26 g, 0.006 mol) in ethanol (100 mL) and water (4 mL) was added sodium cyanide (0.28 g, 0.006 mol, 1 eq.). The yellowish solution was heated to reflux for 8 hours and then cooled, during which time an off-white precipitate was formed. The suspension was filtered under vacuum and the filtrate acidified with HCl gas until the pH was approximately 2. The mixture was then filtered a second time and then the solvent removed in vacuo to leave the crude product as a pale green solid. Flash column chromatography, after absorption of the crude product on to silica, eluting with 0% to 50% EtOAc in heptane gave the binitrile as a colorless solid (0.57 g, 57%).

$^1$H NMR (CDCl$_3$) 400 MHz: 0.99 (3H, s, Me), 1.13 (1H, td, J=13.2, 4.2 Hz), 1.21 (3H, s, Me), 1.32 (2H, m), 1.54 (1H, m), 1.82 (3H, m), 2.15 (1H, m), 2.65 (2H, s, CH$_2$CN). $^{13}$C NMR (CDCl$_3$) 400 MHz: 19.61, 25.17, 30.79, 31.18, 33.77, 34.79, 35.37, 37.92, 46.26, 115.06, 122.19. MS (CI) z/e: 177 (M$^+$+1, 100%), 161 (10), 150 (20), 136 (5), 120 (4), 109 (5). IR (Film) $\upsilon_{max}$ cm$^{-1}$: 2988, 2937, 2869, 2237 (2×CN), 1749, 1456, 1423, 1369, 1202, 1180, 1031, 972.

| Microanalysis: | C$_{11}$H$_{16}$N$_2$: |
|---|---|
| Calc: | C, 74.96; H, 9.15; N, 15.89. |
| Found: | C, 75.08; H, 9.32; N, 15.80. |

Step (iv) Cyanoester

The binitrile (0.50 g, 2.84 mmol) was dissolved in absolute ethanol (20 mL) at room temperature and then cooled to 0° C. Toluene (20 mL) was added to the solution and then the reaction mixture was acidified by passing HCl gas through it at a gentle rate for ca. 45 minutes. The flask was then stoppered and left to stand at room temperature for 24 hours.

The yellow solution was partitioned between ethyl acetate and water and the layers separated. The aqueous layer was extracted with ethyl acetate (3×30 mL), and the combined organics washed with aqueous saturated sodium hydrogen carbonate solution (3×50 mL), brine (3×50 mL), dried (MgSO$_4$), and the solvent removed under reduced pressure to leave a pale yellow liquid (0.59 g, 93%).

$^1$H NMR (CDCl$_3$) 400 MHz: 0.94 (3H, s, Me), 1.16 (3H, m), 1.21 (3H, s, Me), 1.29 (3H, t, J=7.2, CH$_2$CH$_3$), 1.50 (1H, m), 1.65 (1H, dt, J=14.4, 7.6), 1.84 (1H, qt, J=13.3, 3.2), 1.96 (1H, dt, J=13.7, 2.2), 2.16 (1H, m), 2.48 (1H, d, J=15.6, C-2H), 2.54 (1H, d, J=15.6, C-2H), 4.20 (2H, q, J=7.2, CH$_2$CH$_3$). $^{13}$C NMR (CDCl$_3$) 400 MHz: 14.21, 19.65, 25.42, 31.03, 34.04, 34.14, 36.08, 38.44, 46.14, 46.80, 61.02, 123.67, 169.00. MS (CI) z/e: 224 (M$^+$+1, 100%), 196 (12), 178 (35), 136 (13), 109 (12). IR (Film) $\upsilon_{max}$ cm$^{-1}$: 2998 2937, 2868, 2234 (CN), 1738 (C=O), 1457, 1372, 1217, 1181, 1154, 1026.

| Microanalysis: | $C_{13}H_{21}NO_2$: |
|---|---|
| Calc: | C, 69.92; H, 9.48; N, 6.27. |
| Found: | C, 69.63; H, 9.45; N, 6.15. |

Step (v) Lactam

The cyanoester (0.5 g, 2.23 mmol) was hydrogenated in ethanolic ammonia (600 mL) with Raney nickel as catalyst (ca. 0.25 g) at 50° C. and 50 psi for 48 hours.

The catalyst was then removed by filtration through Celite, and the solvent removed in vacuo to leave a greenish crystalline solid.

Flash column chromatography, eluting with 0% to 100% ethyl acetate in heptane, gave the pure lactam as a colorless solid (340 mg, 84%).

$^1$H NMR (CDCl$_3$) 400 MHz: 0.89 (3H, s, Me), 0.92 (3H, s, Me), 1.25 (2H, m), 1.36 (2H, m), 1.51 (3H, m), 1.68 (1H, s), 2.18 (1H, d, J=16.4, CH$_2$NH), 2.24 (1H, d, J=16.8, CH$_2$NH), 3.15 (2H, s, CH$_2$CO). $^{13}$C NMR (CDCl$_3$) 400 MHz: 19.16, 29.88, 30.36, 31.28, 36.57, 39.05, 39.61, 44.58, 49.54, 54.79, 177.72. MS (CI) z/e: 182 (M$^+$+1, 100%), 181 (15), 180 (5), 166 (3). IR (Film) $\upsilon_{max}$ cm$^{-1}$: 3203, 3100 (NH), 2914, 2860, 1698 (C=O), 1486, 1374, 1317, 1289, 1257, 1076.

| Microanalysis: | $C_{11}H_{19}NO$: |
|---|---|
| Calc: | C, 72.88; H, 10.56; N, 7.73. |
| Found: | C, 72.38; H, 10.47; N, 7.56. |

Step (vi) 3,3-Dimethyl Gabapentin Hydrochloride

The lactam (0.3 g, 1.66 mmol) was dissolved in a mixture of HCl (concentrated, 5 mL) and water (5 mL), and the resultant colorless solution heated to reflux for 20 hours. The solution was cooled and then partitioned between water and dichloromethane, and the layers separated. The aqueous layer was washed with dichloromethane (3×20 mL) and the water/HCl removed by rotary evaporation to leave the crude product as an off-white solid. Trituration of this solid with ethyl acetate and filtration of the product gave 3,3-dimethylgabapentin, hydrochloride salt as a colorless solid (140 mg, 42%, 64% based on recovered starting material).

$^1$H NMR (DMSO) 400 MHz: 0.90 (3H, s, Me), 0.92 (3H, s, Me), 1.15–1.49 (8H, m), 2.45 (2H, s, CH$_2$CO$_2$H), 2.90 (2H, br q, J=13.5, CH$_2$NH$_3$), 7.96 (3H, br s, NH$_3$), 12.36 (1H, br s, OH). IR (Film) $\upsilon_{max}$ cm$^{-1}$: 2930, 1728 (C=O), 1272, 1123.

| Microanalysis: | $C_{11}H_{22}NO_2Cl$: |
|---|---|
| Calc: | C, 56.04; H, 9.41; N, 5.94. |
| Found: | C, 55.79; H, 9.61; N, 6.23. |

EXAMPLE 6

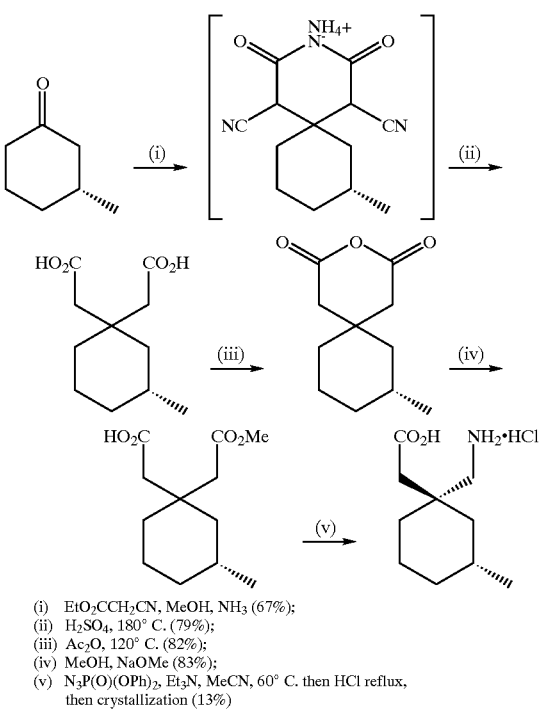

(i) EtO$_2$CCH$_2$CN, MeOH, NH$_3$ (67%);
(ii) H$_2$SO$_4$, 180° C. (79%);
(iii) Ac$_2$O, 120° C. (82%);
(iv) MeOH, NaOMe (83%);
(v) N$_3$P(O)(OPh)$_2$, Et$_3$N, MeCN, 60° C. then HCl reflux, then crystallization (13%)

Steps (i) and (ii)

(R)-3-Methylcyclohexanone (10.92 mL, 89.2 mmol) was dissolved in methanol (25 mL) with ethylcyanoacetate (18.96 mL, 178 mmol) and cooled to 0° C. Ammonia gas was bubbled through the solution for 25 minutes, after which the solution was stoppered and stored at −20° C. After 66 hours, diethyl ether (100 mL) was added to the mixture, and the white solid which formed was filtered off, washed with diethyl ester (2×50 mL), and dried to give 15.71 g (67%) of a white solid.

Without further purification, a sample of the solid (4.0 g, 15.3 mmol) was dissolved in concentrated H$_2$SO$_4$ (40 mL) with gentle warming and allowed to stand overnight. Water (40 mL) was then cautiously added and the resulting mixture heated to 170° C. After 5 hours, all the solid had dissolved. The mixture was cooled to room temperature, diluted with water (200 mL), and extracted with diethyl ether (3×150 mL). The ether extracts were combined, dried over magnesium sulphate, and the solvent removed in vacuo. The oily residue was triturated with heptane to obtain a precipitate which was filtered off and dried to give 2.57 g (79%) of a buff colored solid.

$^1$H NMR (CDCl$_3$) 400 MHz: δ 0.85–0.94 (2H, m), 0.87 (3H, d, J=6 Hz), 1.15 (1H, m), 1.39–1.61 (3H, m), 1.71 (1H, br d, J=12.8 Hz), 1.87 (2H, m), 2.48 (2H, ABq, J=4 Hz), 2.67 (2H, s). MS (ES) z/e: 214 ([M]$^+$, 13%), 213 (100%). IR (thin film) $\upsilon_{max}$ cm$^{-1}$: 1204, 1290, 1413, 1458, 1702, 2924.

| Microanalysis: | $C_{11}H_{18}O_4$: |
|---|---|
| Calc: | C, 61.66; H, 8.47. |
| Found: | C, 61.67; H, 8.51. |

Step (iii) Anhydride

The diacid (2.5 g, 11.68 mmol) was heated to reflux in acetic anhydride (30 mL). After 3 hours, the solvent was removed in vacuo. The residue was dissolved in dichloromethane (50 mL) and washed with saturated aqueous sodium bicarbonate, dried (MgSO$_4$), and the solvent removed in vacuo to obtain 1.83 g (82%) of a brown oil.

$^1$H NMR (CDCl$_3$) 400 MHz: δ 0.84, 0.89 (3H, d, J=6 Hz), 0.98 (1H, m), 1.38–1.60 (4H, m), 1.64–180 (2H, m), 2.53 (2H, s), 2.74 (2H, s). MS (APCI+) z/e: 197 ([MH]$^+$, 100%), 126 (32%). IR (thin film) υ$_{max}$ cm$^{-1}$: 947, 1073, 1181, 1761, 1810, 2925.

| Microanalysis: | C$_{11}$H$_{16}$O$_3$: |
|---|---|
| Calc: | C, 67.32; H, 8.22. |
| Found: | C, 66.98; H, 8.07. |

Step (iv) Half Ester, Cis/trans Mixture

The anhydride (1.865 g, 9.5 mmol) was dissolved in dry methanol (10 mL) with sodium methoxide (0.5 M in MeOH, 20 mL, 10 mmol) and stirred at room temperature. After 3 hours the solvent was removed in vacuo and the residue partitioned between ethyl acetate (150 mL) and 1N HCl (50 mL). The organic phase was separated and the aqueous phase re-extracted with ethyl acetate (2×100 mL). The organic extracts were combined, dried (MgSO$_4$), and the solvent removed in vacuo to give 1.8 g (83%) of a pale brown oil which contained a –1:1 mixture of the cis and trans isomers.

$^1$H NMR (CDCl$_3$) 400 MHz: δ 0.85–0.93 (2H, m); 0.86 (3H, d, J=6 Hz); 1.17 (1H, m); 1.39–1.62 (3H, m); 1.64–1.80 (3H, m); 2.48 (2H, m); 2.64–2.65 (2H, 2×s one from each isomer). MS (ES–) z/e: 227 ([M-H]$^+$, 100%). IR (thin film) υ$_{max}$ cm$^{-1}$: 1163, 1194, 1440, 1705, 1738, 2926, 3200.

| Microanalysis: | C$_{12}$H$_{20}$O$_4$: |
|---|---|
| Calc: | C, 63.13; H, 8.83. |
| Found: | C, 63.29; H, 8.83. |

Step (v) (1-Aminomethyl-3-methyl-cyclohexyl)-acetic Acid [(1s-(1α,3β)]

The mixture of half ester isomers (515 mg, 2.26 mmol) was dissolved in acetone (6 mL) and cooled to –10° C. Triethylamine (377 μL, 2.7 mmol) was added followed by ethyl chloroformate (259 μL, 2.7 mmol). The mixture was stirred at –10° C. for 40 minutes, after which a solution of sodium azide (220 mg, 3.39 mmol) in water (1 mL) was added and the mixture allowed to warm to 0° C. After 40 minutes, the mixture was poured into ice cold water (20 mL) and extracted with ice cold toluene (3×20 mL). The toluene extracts were combined and dried over magnesium sulfate at 0° C. The toluene solution was then added dropwise into a flask preheated to 180° C. in an oil bath at 180° C. The solvent was removed via distillation. Once the addition was complete, the mixture was stirred at 180° C. for a further 20 minutes, until all the solvent had been removed. Dioxane (5 mL) and concentrated HCl (5 mL) were then added and the mixture refluxed for 3 hours. The mixture was then cooled to room temperature, diluted with water (30 mL), and washed with dichloromethane (2×30 mL). The aqueous phase was collected and the solvent removed in vacuo to give a brown gum, which was triturated with ethyl acetate to give a buff colored solid. The solid was recrystallized from a mixture of methanol, ethyl acetate, and heptane to yield 35 mg (7%) of a white solid.

$^1$H NMR (d$_6$ DMSO) 400 MHz: δ 0.70–0.88 (2H, m), 0.83 (3H, d, J=6 Hz), 1.06–1.17 (1H, m), 1.36–1.69 (6H, m), 2.44 (2H, s), 2.84 (2H, s), 7.92 (4H, br s). MS (ES+) z/e: 186 ([MH-HCl]$^+$, 100%). IR (thin film) υ$_{max}$ cm$^{-1}$: 1211, 1408, 1709, :2925, 3200.

| Microanalysis: | C$_{10}$H$_{20}$NO$_2$Cl · 0.25 H$_2$O: |
|---|---|
| Calc: | C, 53.09; H, 9.13; N, 6.19; Cl, 15.67. |
| Found: | C, 53.24; H, 9.26; N, 6.23; Cl, 15.43. |

EXAMPLE 7

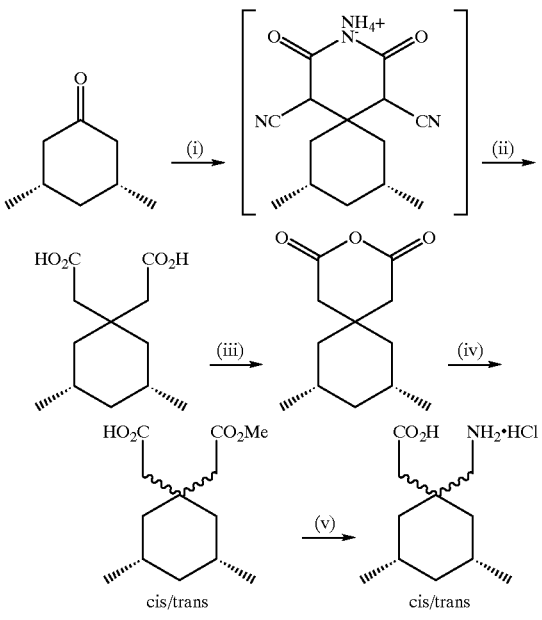

(i) EtO$_2$CCH$_2$CN, MeOH, NH$_3$;
(ii) H$_2$SO$_4$, 180° C.;
(iii) Ac$_2$O, 120° C.;
(iv) MeOH, NaOMe;
(v) EtOCOCl, NET$_3$, then NaN$_3$, then heat, then HCl reflux Cis/trans 3.5-dimethyl Gabapentin Steps (i) and (ii) Diacid Cis-3,5-dimethyl-cyclohexanone (11.24 g, 89.2 mmol) was dissolved in methanol (25 mL) ethyl cyanoacetate (18.96 mL, 178.2 mmol) and cooled to 0° C. Ammonia gas was then bubbled through the solution for 30 minutes. The solution was then stored at –20° C. After 66 hours, the solid was filtered off, washed with ether, and dried to yield 18.46 g (75%) of a white solid.

Without further purification, a portion of the solid prepared above (6.0 g, 21.7 mmol) was dissolved in concentrated sulphuric acid (40 mL) with warming and left to stand overnight. Water (40 mL) was then cautiously added and the resulting solution heated to 180° C. After 5 hours, the mixture was cooled to room temperature, diluted with water (200 mL), and extracted with diethyl ether (3×150 mL). The organic extracts were combined, washed with brine, dried (MgSO$_4$), and the solvent removed in vacuo. The residue was triturated with heptane to obtain a solid which was recrystallized from a dichloromethane/heptane mixture to obtain 3.122 g (63%) of a buff colored solid.

$^1$H NMR (CDCl$_3$) 400 MHz: δ 0.49 (1H, m), 0.80 (2H, m), 0.87 (6H, d, J=6 Hz), 1.55–1.76 (3H, m), 1.85 (2H, br, d, J=13.2 Hz), 2.50 (2H, s), 2.67 (2H, s). MS (ES) z/e: 228 ([M]$^+$, 14%), 227 ([M-H]$^+$, 100%). IR (thin film) υ$_{max}$ cm$^{-1}$:

893, 1147, 1208, 1284, 1312, 1337, 1407, 1450, 1699, 2846, 2914, 2947, 3100.

| Microanalysis: | $C_{12}H_{20}O_4$: |
|---|---|
| Calc: | C, 63.13; H, 8.83. |
| Found: | C, 63.22; H, 8.95. |

Step (iii) Anhydride

The diacid (3.0 g, 13.16 mmol) was dissolved in acetic anhydride (40 mL) and heated to reflux. After 3 hours, the mixture was cooled to room temperature and the solvent removed in vacuo. The residue was dissolved in dichloromethane (150 mL) and washed once with saturated aqueous sodium bicarbonate. The organic phase was separated, dried (MgSO$_4$), and the solvent removed in vacuo to obtain 2.60 g (94%) of a brown oil which solidified on standing.

$^1$H NMR (CDCl$_3$) 400 MHz: δ 0.53 (1H, m), 0.81–0.96 (2H, m, and 6H, d, J=6 Hz), 1.43–1.71 (4H, m), 1.76 (1H, m), 2.54 (2H, s), 2.73 (2H, s). MS (APCI+) z/e: 211 ([MH]$^+$, 100%). IR (thin film) $\upsilon_{max}$ cm$^{-1}$: 950, 1073, 1183, 1459, 1756, 1767, 1812, 2910, 2952.

| Microanalysis: | $C_{12}H_{18}O_3$: |
|---|---|
| Calc: | C, 68.55; H, 8.75. |
| Found: | C, 63.32; H, 8.75. |

Step (iv) Cis/trans Half Ester

The anhydride (2.556 g, 12.17 mmol) was dissolved in dry methanol (15 mL) and stirred with in vacuo and the residue partitioned between 1N HCl (150 mL) and ethyl acetate (150 mL). The organic phase was separated, washed with brine, dried (MgSO$_4$), and the solvent removed in vacuo to give a yellow oil. This was purified by flash chromatography (silica, ethyl acetate:heptane, 1:1) to give 2.68 g (91%) of a colorless oil.

$^1$H NMR (CDCl$_3$) 400 MHz: δ 0.47 (2H, m), 0.82 (4H, m), 0.87 (12H, d, J=6 Hz), 1.57–1.80 (10H, m), 2.46 (2H, s, isomer A), 2.48 (2H, s, isomer B), 2.63 (2H, s, isomer B), 2.64 (2H, s, isomer A), 3.67 (6H, s). MS (ES–) z/e: 241 ([M-H]$^+$, 100%). IR (thin film) $\upsilon_{max}$ cm$^{-1}$: 1163, 1197, 1437, 1459, 1706, 1736, 2913, 2951, 3100.

| Microanalysis: | $C_{13}H_{22}O_4$: |
|---|---|
| Calc: | C, 64.44; H, 9.15. |
| Found: | C, 64.17; H, 9.17. |

Step (v) Cis/trans-3,5-Dimethyl Gabapentin

The cis/trans mixture of half esters (1.09 g, 4.5 mmol) was dissolved in acetone (15 mL) and cooled to −10° C. Triethylamine (predried over lithium aluminum hydride) (660 μL, 4.74 mmol) was then added followed by ethyl chloroformate (453 μL, 4.764 mmol). After 40 minutes at 10° C., a solution of sodium azide (337 mg, 5.19 mmol) in water (2.5 mL) was added and the mixture allowed to warm to 0° C. After 40 minutes, the mixture was poured into ice cold water (30 mL) and extracted with ice cold toluene (3×20 mL). The organic extracts were combined, dried (MgSO$_4$), and stored at 0° C. The toluene solution was then added dropwise to a flask set up for distillation in an oil bath set at 180° C. The solvent was removed by distillation during the additions. After the addition was complete, the mixture was stirred at 180° C. for 1 hour, after which a gentle stream of nitrogen was passed through the apparatus to remove the last traces of solvent. Hydrochloric acid (75% v/v, 20 ml,) was then added cautiously, and the resulting solution refluxed for 3 hours. The mixture was cooled to room temperature and stored at room temperature overnight. The mixture was diluted with water (20 mL) and extracted with dichloromethane (2×15 mL). The aqueous phase was collected and the solvent removed in vacuo. The residue was triturated with ethyl acetate to obtain 255 mg (24%) of a white solid.

$^1$H NMR (d$_6$ DMSO) 400 MHz: δ 0.46 (2H, m), 0.76–0.90 (16H, m), 1.50–1.70 (10H, m), 2.30 (2H, s, isomer A), 2.44 (2H, s, isomer B), 2.84 (2H, s, isomer B), 3.00 (2H, s, isomer A), 7.91 (6H, br s), 12.40 (2H, br s). MS (ES+) z/e: 200 ([MH-HCl]$^+$, 100%). IR (thin film) $\upsilon_{max}$ cm$^{-1}$: 1201, 1458, 1715, 2949, 3200.

| Microanalysis: | $C_{11}H_{22}NO_2Cl$: |
|---|---|
| Calc: | C, 56.04; H, 9.41; N, 5.94. |
| Found: | C, 55.75; H, 9.46; N, 5.87. |

EXAMPLE 8

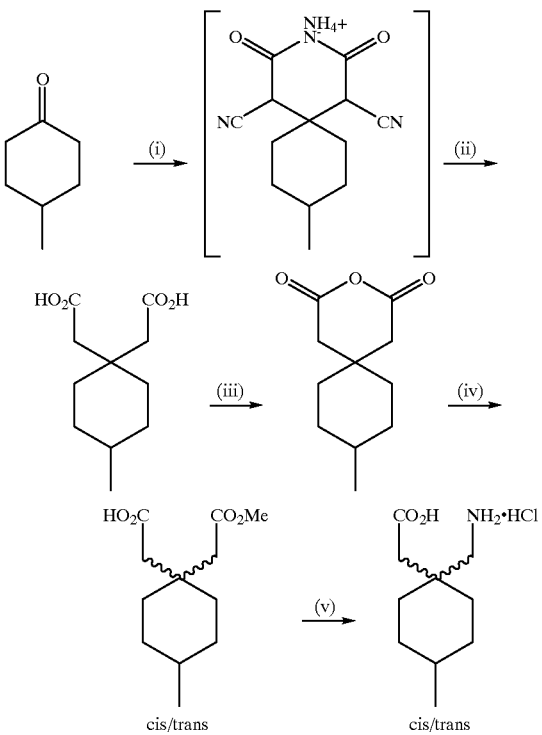

cis/trans     cis/trans (i) EtO$_2$CCH$_2$CN, MeOH, NH$_3$;
(ii) H$_2$SO$_4$, 180° C.;
(iii) Ac$_2$O, 120° C.;
(iv) MeOH, NaOMe;
(v) EtOCOCl, NET$_3$, then NaN$_3$, then heat, then HCl reflux Cis/trans 4-methyl Gabapentin Steps (i) and (ii) Diacid 4-Methylcyclohexanone (5 mL, 40.74 mmol) was dissolved in methanol (15 mL) with ethyl cyanoacetate (8.67 mL, 81.48 mmol) and cooled to 0° C. Ammonia gas was bubbled through the solution for 25 minutes, after which the solution was stoppered and stored at −20° C. After 20 hours, diethyl ether (100 mL) was added to the mixture, and the white solid which formed was filtered off, washed with diethyl ether (2×50 mL), and dried to give 7.51 g (70%) of a white solid.

Without further purification, a sample of the solid (4.0 g, 15.3 mmol) was dissolved in concentrated $H_2SO_4$ (40 mL) with gentle warming and allowed to stand overnight. Water (40 mL) was then cautiously added and the resulting mixture heated to 170° C. After 3 hours, all the solid had dissolved. The mixture was cooled to room temperature, diluted with water (150 mL), and extracted with diethyl ether (3×100 mL). The ether extracts were combined, dried over magnesium sulphate, and the solvent removed in vacuo. The oily residue was triturated with heptane to obtain a precipitate which was filtered off and dried to give 2.3 g (73%) of a buff colored solid.

$^1$H NMR (d$_6$ DMSO) 400 MHz: δ 0.87 (3H, d, J=6 Hz); 1.1 (2H, m); 1.27 (3H, m); 1.44 (2H, m); 1.70 (2H, br d, J=13 Hz); 2.34 (2H, s); 2.45 (2H, s). MS (ES−) z/e: 214 ([M]$^+$, 13%), 213 ([M-H]$^+$, 100%). IR (thin film) $\upsilon_{max}$ cm$^{-1}$: 917, 1183, 1215, 1289, 1349, 1399, 1455, 1704, 2858, 2925, 3100.

| Microanalysis: | $C_{11}H_{18}O_4$: |
|---|---|
| Calc: | C, 61.66; H, 8.47. |
| Found: | C, 61.54; H, 8.47. |

Step (iii) Anhydride

The diacid (2.30 g, 10.75 mmol) was heated to reflux in acetic anhydride (30 mL). After 3.5 hours, the solvent was removed in vacuo. The residue was dissolved in dichloromethane (50 mL) and washed with saturated aqueous sodium bicarbonate, dried (MgSO$_4$), and the solvent removed in vacuo to obtain 2.07 g (98%) of a brown oil which solidified on standing.

$^1$H NMR (CDCl$_3$) 400 MHz: δ 0.93 (3H, d, J=6 Hz), 1.07 (2H, m), 1.37 (3H, m), 1.49–1.71 (4H, m), 2.56 (2H, s), 2.72 (2H, s). MS (APC1+) z/e: 197 ([MH]$^+$, 100%). IR (thin film) $\upsilon_{max}$ cm$^{-1}$: 953, 1064, 1183, 1241, 1455, 1761, 1810, 2924.

| Microanalysis: | $C_{11}H_{16}N_3$: |
|---|---|
| Calc: | C, 67.32; H, 8.22. |
| Found: | C, 67.41; H, 8.29. |

Step (iv) Cis/trans Half Ester

The anhydride (2.06 g, 10.5 mmol) was dissolved in dry methanol (40 mL) and stirred with sodium methoxide (624 mg, 11.55 mmol). After 4 hours, the solvent was removed in vacuo and the residue partitioned between 1N HCl (150 mL) and dichloromethane (150 mL). The organic phase was separated, washed with brine, dried (MgSO$_4$), and the solvent removed in vacuo to give a yellow oil. This was purified by flash chromatography (silica, ethyl acetate:heptane, 1:1) to give 1.98 g (83%) of a colorless oil.

$^1$H NMR (CDCl$_3$) 400 MHz: δ 0.83–0.92 (2H, m), 0.91 (6H, d, J=6 Hz), 1.14 (4H, m), 1.21–1.42 (4H, m), 1.54 (4H, m), 1.77 (4H, m), 2.49 (2H, s, isomer A), 2.50 (2H, s, isomer B), 2.62 (2H, s, isomer B), 2.64 (2H, s, isomer A), 3.66 (3H, s, isomer A), 3.67 (3H, s, isomer B). MS (ES−) z/e: 227 ([M-H]$^+$, 100%). IR (thin film) $\upsilon_{max}$ cm$^{-1}$: 1162, 1193, 1434, 1699, 1731, 2922, 3200.

| Microanalysis: | $C_{12}H_{20}O_4$: |
|---|---|
| Calc: | C, 63.13; H, 8.83. |
| Found: | C, 63.12; H, 8.71. |

Step (v) Cis/trans 4-methyl Gabapentin

The cis/trans mixture of half esters (1.90 g, 8.3 mmol) was dissolved in acetone (20 mL) and cooled to −10° C. Triethylamine (predried over lithium aluminium hydride) (1.21 mL, 8.7 mmol) was then added followed by ethyl chloroformate (832 μL, 8.7 mmol). After 50 minutes at −10° C., a solution of sodium azide (630 mg, 9.69 mmol) in water (5 mL) was added and the mixture allowed to warm to 0° C. After 40 minutes, the mixture was poured into ice cold water (50 mL) and extracted with ice cold toluene (3×50 mL). The organic extracts were combined, dried (MgSO$_4$), and kept at 0° C. The toluene solution was then added dropwise to a flask set up for distillation in an oil bath set at 180° C. The solvent was removed by distillation during the addition. After the addition was complete, the mixture was stirred at 180° C. for 1 hour, after which a gentle stream of nitrogen was passed through the apparatus to remove the last traces of solvent. Hydrochloric acid (75% v/v, 40 mL) was then added cautiously, and the resulting solution refluxed for 3 hours. The mixture was cooled to room temperature and sorted at room temperature overnight. The mixture was diluted with water (30 mL) and extracted with dichloromethane (3×30 mL). The aqueous phase was collected and the solvent removed in vacuo. The residue was triturated with ethyl acetate to obtain 590 mg (32%) of a white solid.

$^1$H NMR (d$_6$ DMSO) 400 MHz: δ 0.87 (6H, d, J=6 Hz), 1.07 (4H, m), 1.19–1.40 (6H, m), 1.41–1.58 (6H, m), 1.61 (2H, m), 2.32 (2H, s, isomer A), 2.44 (2H, s, isomer B), 2.85 (2H s, isomer B), 2.99 (2H, s, isomer A), 7.96 (6H, br s), 12.36 (2H br s). MS (ES+) z/e: 186 ([MH-HCl]$^+$, 100%). IR (thin film) $\upsilon_{max}$ cm$^{-1}$: 1195, 1404, 1457, 1506, 1607, 1712, 2924, 3200.

| Microanalysis: | $C_{10}H_{20}NO_2Cl$: |
|---|---|
| Calc: | C, 54.17 H, 9.09; N, 6.32. |
| Found: | C, 54.13; H, 9.18; N, 6.45. |

What is claimed is:

1. A compound of formula

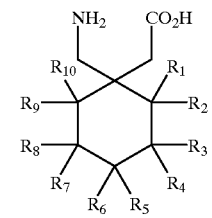

I a pharmaceutically acceptable salt thereof or a prodrug thereof wherein $R_1$ to $R_{10}$ are each independently selected from straight or branched alkyl of from 1 to 6 carbon atoms, unsubstitutued or substituted benzyl or phenyl which substituents are selected from halogen, alkyl, alkoxy, hydroxy, carboxy, carboalkoxy, trifluoromethyl, and nitro, and any $R_1$ to $R_{10}$, which is not one of the above, is hydrogen and at least one of $R_1$ to $R_{10}$ is not hydrogen.

2. A compound according to claim 1 wherein $R_1$ to $R_{10}$ is selected from methyl, ethyl, propyl, butyl straight or branched.

3. A compound of formula I

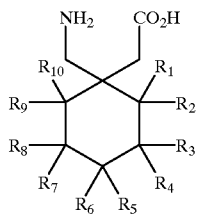

a pharmaceutically acceptable salt thereof or a prodrug thereof
wherein $R_1$ to $R_4$ and $R_6$ to $R_{10}$ are hydrogen and
$R_5$ is tert-butyl.

4. A compound according to claim 1 wherein $R_3$ is methyl.

5. A compound according to claim 1 selected from a compound of Formula I, wherein $R_1$ is methyl or $R_5$ is methyl.

6. A compound of formula I

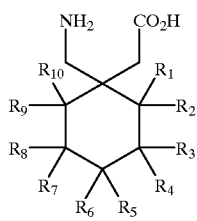

a pharmaceutically acceptable salt thereof or a prodrug thereof
wherein $R_1$ to $R_4$ and $R_6$ to $R_{10}$ are hydrogen and
$R_5$ is isopropyl.

7. A compound according to claim 1 selected from
(1-aminomethyl-3-methyl-cyclohexyl)-acetic acid and
(1-aminomethyl-3-methylcyclohexyl)-acetic acid [1R-(1α,3β)].

8. A compound according to claim 1 selected from
(1-aminomethyl-4-tert-butyl-cyclohexyl)-acetic acid and
cis (1-aminomethyl-4-methyl-cyclohexyl)-acetic acid.

9. A compound and named
(1-aminomethyl-3-methyl-cyclohexyl)-acetic acid [1s-(1α,3β)].

10. A compound selected from
(1-aminomethyl-3-methyl-cyclohexyl)-acetic acid methyl ester monohydrochloride;
[1-(acetylamino-methyl)-3-methyl-cyclohexyl]-acetic acid; and
[2-(1-Aminomethyl-3-methyl-cyclohexyl)-acetylamino]-acetic acid monohydrochloride.

11. A compound according to claim 1 selected from
(±)-(1-aminomethyl-3,3-dimethyl-cyclohexyl)-acetic acid;
(1-aminomethyl-3,3,5,5-tetramethyl-cyclohexyl)-acetic acid; and
(1-aminomethyl-4-methyl-cyclohexyl)-acetic acid.

12. A pharmaceutical composition comprising a therapeutically effective amount of a compound according to claim 1 and a pharmaceutically acceptable carrier.

13. A method for treating epilepsy comprising administering a therapeutically effective amount of a compound according to claim 1 to a mammal in need of said treatment.

14. A method for treating faintness attacks, hypokinesia, and cranial disorders comprising administering a therapeutically effective amount of a compound according to claim 1 to a mammal in need of said treatment.

15. A method for treating neurodegenerative disorders comprising administering a therapeutically effective amount of a compound according to claim 1 to a mammal in need of said treatment.

16. A method for treating depression comprising administering a therapeutically effective amount of a compound according to claim 1 to a mammal in need of said treatment.

17. A method for treating anxiety comprising administering a therapeutically effective amount of a compound according to claim 1 to a mammal in need of said treatment.

18. A method for treating panic comprising administering a therapeutically effective amount of a compound according to claim 1 to a mammal in need of said treatment.

19. A method for treating pain comprising administering a therapeutically effective amount of a compound according to claim 1 to a mammal in need of said treatment.

20. A method for treating neuropathological disorders comprising administering a therapeutically effective amount of a compound according to claim 1 to a mammal in need of said treatment.

* * * * *